United States Patent
Von Der Eltz et al.

[11] Patent Number: 5,926,269
[45] Date of Patent: Jul. 20, 1999

[54] OPTICAL PROBE WITH SENSOR MADE OF OPTICAL POLYMER

[75] Inventors: Andreas Von Der Eltz, Frankfurt am Main; Dirk Buchwald, Selters; Andreas Brockmeyer, Liederbach; Marion Walter, Weilburg, all of Germany

[73] Assignee: Dystar Textilfarben GmbH & Co., Germany

[21] Appl. No.: 08/981,197

[22] PCT Filed: Jun. 13, 1996

[86] PCT No.: PCT/EP96/02550

§ 371 Date: Mar. 13, 1998

§ 102(e) Date: Mar. 13, 1998

[87] PCT Pub. No.: WO97/00437

PCT Pub. Date: Jan. 3, 1997

[30] Foreign Application Priority Data

Jun. 14, 1995 [DE] Germany ............................ 195 21 628

[51] Int. Cl.⁶ .................................................. G01N 21/01
[52] U.S. Cl. ........................ 356/300; 356/326; 250/339.11
[58] Field of Search .................................... 356/300, 326, 356/328, 244, 246; 250/339.11

[56] References Cited

U.S. PATENT DOCUMENTS 5,170,056  12/1992  Berard et al. ................... 250/339.11
5,396,325   3/1995  Carome et al. .................. 356/128

FOREIGN PATENT DOCUMENTS

| 0221011 | 5/1987 | European Pat. Off. |
|---|---|---|
| 0206433 | 5/1993 | European Pat. Off. |
| 4038054 | 6/1992 | Germany |
| 4214594 | 11/1993 | Germany |
| WO 93/20240 | 10/1993 | WIPO |
| WO 94/28395 | 12/1994 | WIPO |

OTHER PUBLICATIONS

Wilks, P. A., Jr., *InternationalLaboratory*: Jul./Aug. pp. 47–54 (1980).

"Proceedings of the Annual International Conference of the IEEE Eng. in Med. and Biol. Soc.", vol. 14, pp. 171–172, Pub. date: Oct. 29, 1992, Ed'd by J.P.Morucci et al.

*Primary Examiner*—F. L. Evans
*Attorney, Agent, or Firm*—Connolly & Hutz

[57] ABSTRACT

The invention relates to an ATR spectrometer, containing an optical probe having a sensor made of transparent material and a feed line and an exit line for light, wherein the sensor contains an optical polymer or a mixture of different optical polymers. The probe of the spectrometer according to the invention essentially has the advantages that it is inexpensive and extremely flexible, and that it can be matched to the concentration range of the solution to be examined, which makes it possible to fill the gaps in terms of measurable concentrations between conventional transmission spectroscopy and prior ATR spectroscopy.

9 Claims, 6 Drawing Sheets

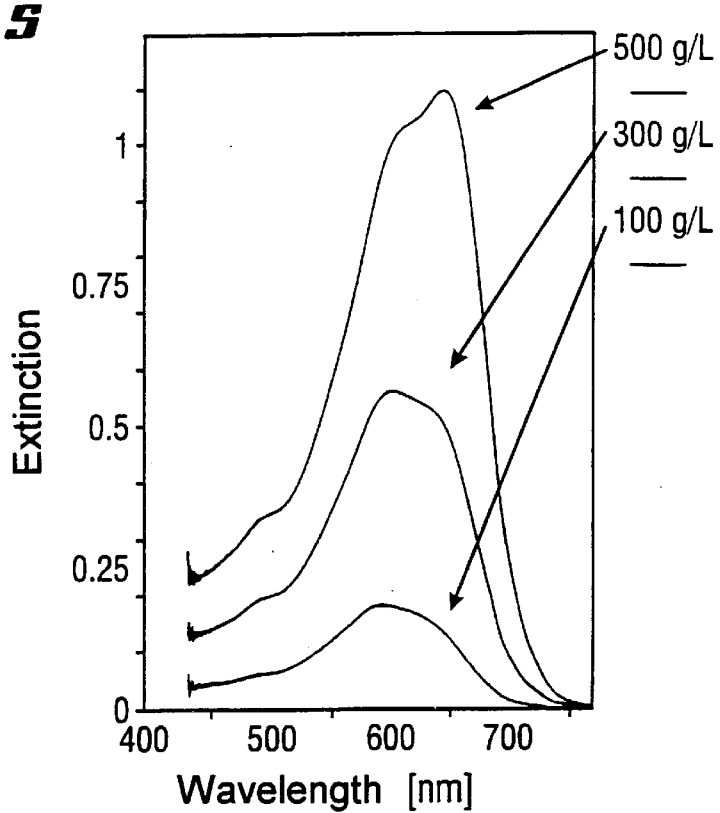
Fig. 5
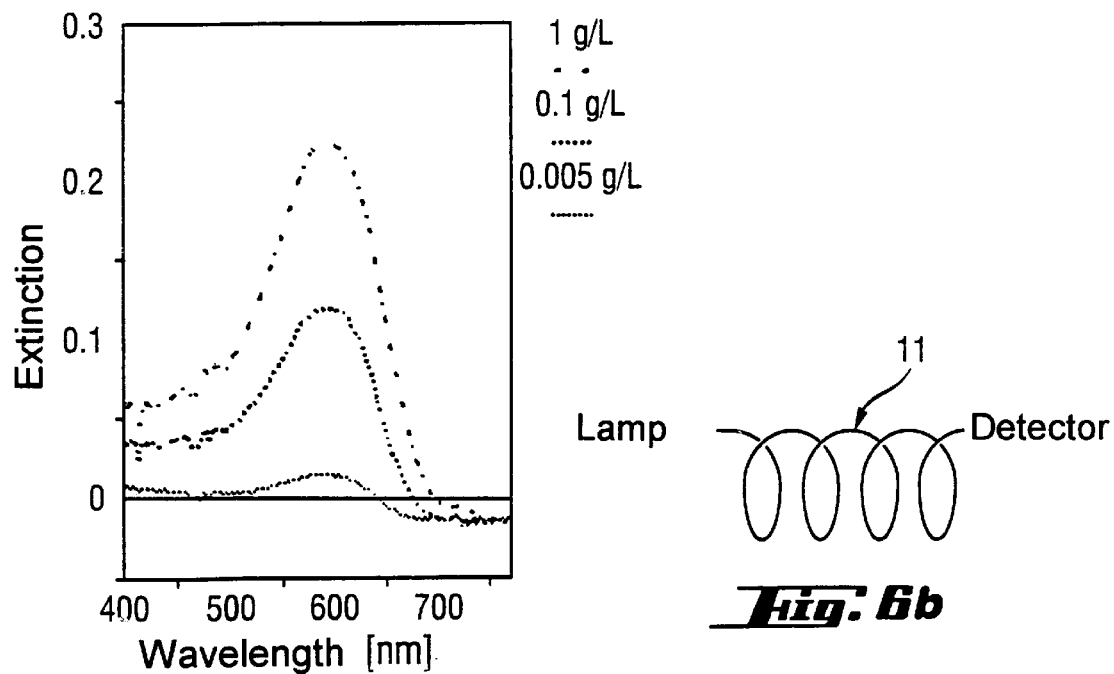
Fig. 6a
Fig. 6b

OPTICAL PROBE WITH SENSOR MADE OF OPTICAL POLYMER

The invention relates to an ATR spectrometer, containing an optical probe, and to a method of analyzing liquid media which may or may not contain a solid.

Methods, spectrometers and probes of the abovementioned type are known, for example, from EP 0 221 011 A 2, from N. J. Harrick: Internal Reflection Spectroscopy, J. Wiley & Sons, New York 1976 and from the review article by P. A. Wilks in International Laboratory July/August 1989, p. 47–55. The publications by Harrick and Wilks describe "Attenuated Total Reflection" (ATR) spectroscopy. In brief, ATR spectroscopy operates as follows: A probe having a transparent sensor made of high-index material is brought into contact with a liquid medium having lower refractive index. In the sensor, a light beam is guided by total reflection at the interface between the sensor and the medium. At each reflection from the interface, the light enters the medium as a so-called transversely damped wave and interacts with the molecules in the medium, some of the light being absorbed and the rest being scattered back into the sensor. The light beam guided in the probe then has a deficit in the excitation energy range of particular molecules, and can therefore be analyzed with a spectrometer and used to identify these molecules. In contrast to conventional transmission spectroscopy, in which light is passed through glass cuvettes which are a few mm thick, the measurements in ATR spectroscopy relate only to a very thin layer around the probe. The thickness of this layer depends on the wavelength, the refractive indices, the angle of incidence and the polarization, and is of the order of magnitude of one wavelength of the absorbed light. The fact that the measuring layer is very thin makes it possible to take measurements in highly concentrated solutions, while these measurements can only be taken using transmission spectroscopy after the solutions have been diluted several times. EP 221 011 describes a method which, using ATR spectroscopy, makes it possible to measure highly concentrated dyestuff solutions and dispersions. In addition to high-index glasses, for example heavy flint glass, aluminum oxide (sapphire), diamond, strontium titanate, titanium oxide, zirconium oxide and quartz glass are also mentioned as materials for the relevant sensors. Particular emphasis is placed on the good measurement results obtained using sapphire prisms.

Probes having sensors made of these materials have the disadvantages that they are comparatively expensive and rigid and, depending on the material and design, can break easily.

The invention provides an improvement to this situation.

According to the invention, this is achieved in that the sensor contains an optical polymer or a mixture of different optical polymers.

The invention therefore relates to an ATR spectrometer, containing an optical probe having a sensor made of transparent material and a feed line and an exit line for light, wherein the sensor contains an optical polymer or a mixture of different optical polymers.

The spectrometer according to the invention is outstandingly suitable for methods of analyzing liquid media which may or may not contain a solid, in particular dyestuff solutions. The spectrometer is also particularly suitable for the analysis of blood, since the sensor is employed sterilized and, after use, can be disposed of without entailing great expense. The optical (transparent) polymer may be present as an essentially pure material, but may also be a mixture of different optical polymers.

Suitable polymers include transparent polymers such as polymethyl methacrylate, polycarbonates, polystyrenes, polyolefins, polyesters, polysulfones, polyether sulfones, polyether imides, polyarylates, polyamides, polyester carbonates, copolymers such as, for example, methyl methacrylate and n-pentafluoropropyl methacrylate, and polymer blends of polymethyl methacrylate/polyvinylidene fluoride. Polymethyl methacrylate is preferably used.

In one particular embodiment, the sensor is in the form of a fiber which can simultaneously be used as an optical waveguide for the light to be fed in and to exit, and as a sensor, it also being possible for the sensor to be composed of a plurality of fibers. In this case, a protective jacket which may be present, as well as a cladding which may be present, should be removed at the points on the fiber which are to act as a sensor. The term "cladding" is intended to mean a chemical modification to the polymer surface (for example fluorination), or the application of a different polymer which is intended to protect the fiber. Removal is carried out by dissolving with suitable solvents, for example ethyl acetate or petroleum ether. The fiber diameters which are preferred lie between 0.2 and 10 mm, preferably between 0.5 and 5 mm. The number of times which the light is reflected in the fiber can be set by selecting the length of the cladding-free zone. It is in this way possible to match the sensor to the concentration range of the solution to be examined. Because of the material which is used, and the form which the fiber has, the sensor is extremely flexible and can, for example be wound into the shape of a spiral, also be used with a relatively great length in relatively small measuring cells. The feed line and exit line for the light may be part of the fiber. The form of a fiber also opens up the possibility of connecting the sensor to another fiber, preferably a glass fiber, by means of which the light can be carried over long distances virtually without loss. The connection may be designed as a plug connection and connect fibers having different diameters. FSMA connectors are preferably used for this. In one special embodiment of the probe according to the invention, the fiber is mirrored at one end and the feed line and the exit line for the light are arranged at the other end. It is also possible for a glass fiber to be fused into the polymer fiber. The form of a fiber also allows the probe to be introduced into a continuous flow cell. The probe according to the invention further has the surprising property that, when the sensor is in the form of a fiber or a straight or curved rod, the light can be guided in an angular range of from 0 to 40°, in particular from 5 to 35° with respect to the axis of the fiber or rod, without entailing problems for the analysis.

Spectrometers which are suitable include customary UV/VIS/NIR spectrometers which, for example, may be designed as grating spectrometers, linear diode array spectrometers or a CCD (Charge Coupled Device) spectrometer. The spectrometer according to the invention can also be combined as desired with one or more features from the embodiments. However, the probe with the optical polymer may itself represent an invention.

The probe of the spectrometer according to the invention essentially has the advantages that it is inexpensive and extremely flexible, and that it can be matched to the concentration range of the solution to be examined, which makes it possible to fill the gaps in terms of measurable concentrations between conventional transmission spectroscopy and prior ATR spectroscopy.

The probe of the spectrometer according to the invention will be described in more detail below with reference to the illustrative embodiments schematically represented in FIGS. 1 to 4, in which:

FIG. 5 shows the spectra of a solution of black dyestuff using the probe of FIG. 3.

Figure 7A:
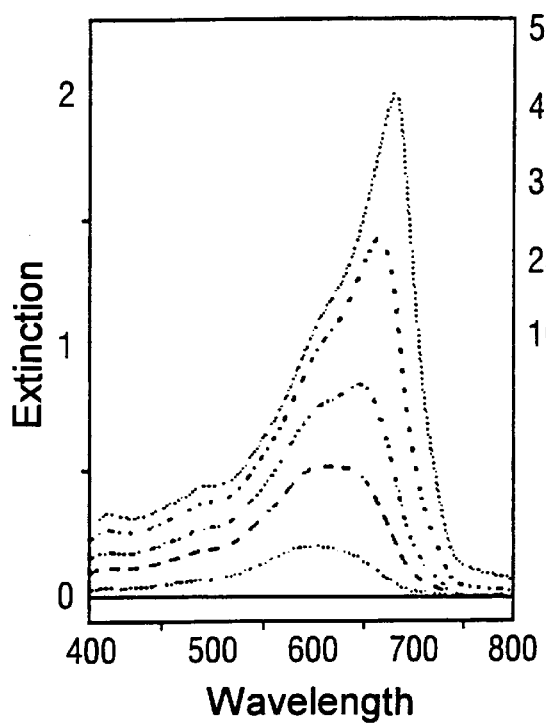
Figure 7B:
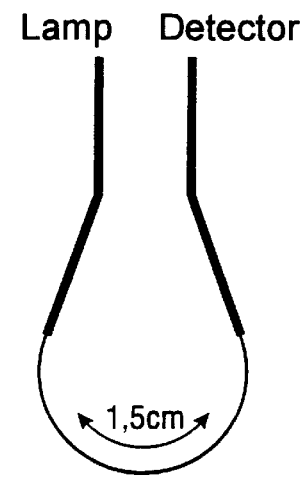
Figure 8A:
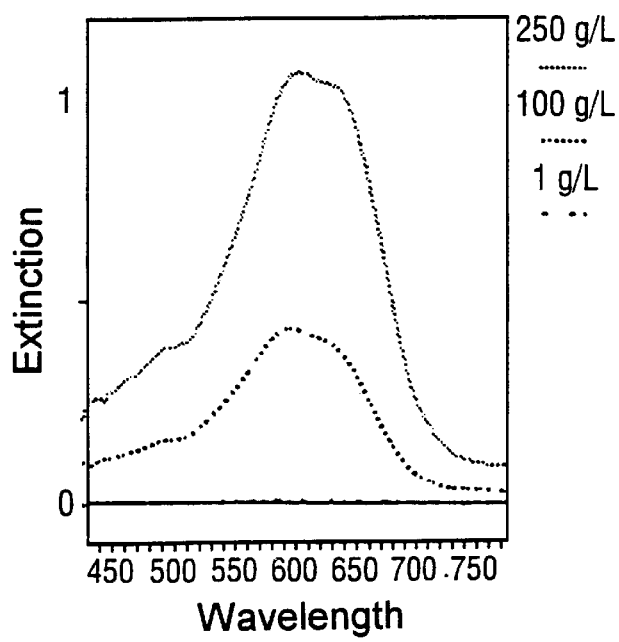
Figure 8B:
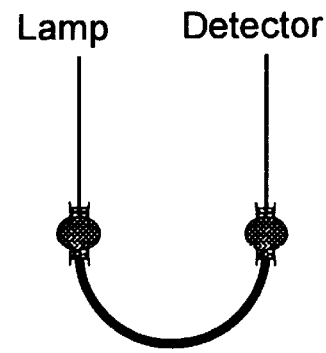

FIGS. 6a, 7a, and 8a show the spectra of a black dyestuff using the probes of FIGS. 6b, 7b and 8b, respectively.

FIGS. 6b, 7b, and 8b show additional embodiments the probe.

Figure 1:
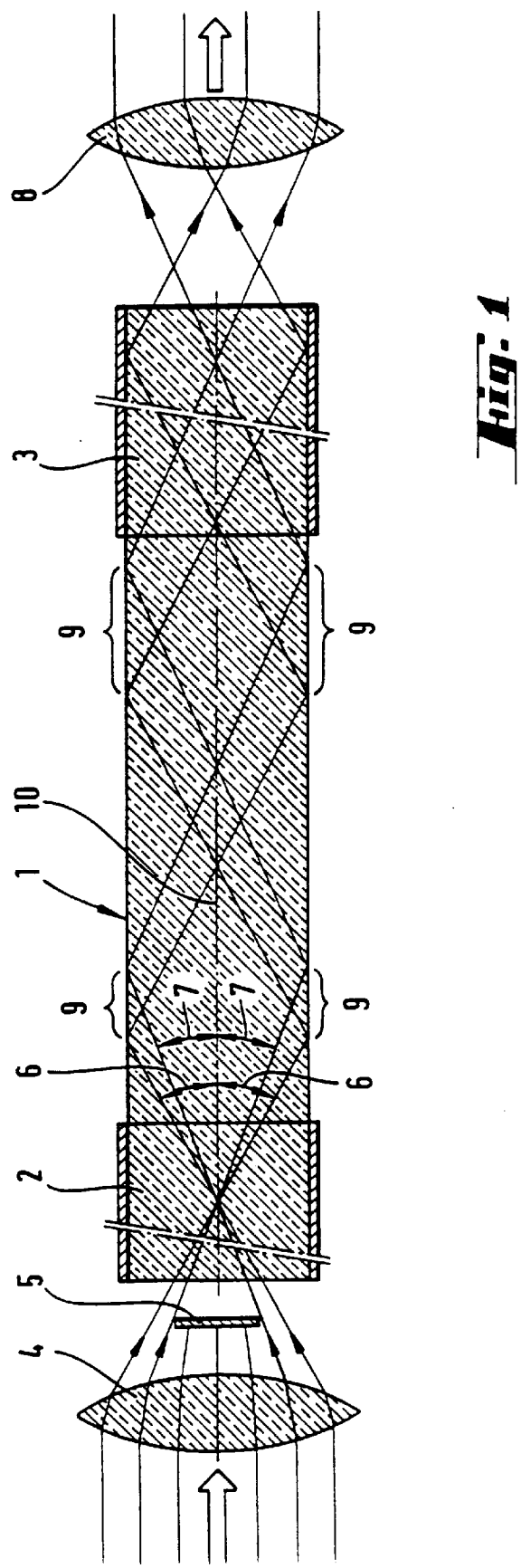
FIG. 1 shows a probe with light guiding according to the invention.

FIG. 1 shows a rotationally symmetric probe, essentially comprising a sensor, in the form of a fiber 1 made of an optical polymer, of a feed line 2 and an exit line 3 for the light. The light is focused by a lens 4 and fed into the fiber 1 via the feed line 2, it being possible for part of the light to be stopped out by a mask 5. By means of this, in accordance with the method according to the invention, the light can be guided through the fiber in an angular range which is bounded by the angles 6 and 7 with respect to the axis 10 of the fiber, and which depends on the dimensions of the lens 4 and the mask 5. At the end of the fiber, the light enters the exit line 3 and is delivered thereby to a lens 8 which, for its part, forwards it to the analysis part (not shown) of the spectrometer. The light interacts with the medium to be examined and the illuminated interface 9 which the fiber forms with the medium. It can be seen that the total area 9 increases disproportionately with the number of times the light is reflected, this being in turn determined by the fiber length and the angular range. The probe can therefore be matched to a broad range of concentrations, since both the lower limit and the upper limit of the analyzable concentration range decrease as the length increases.

Figure 2:
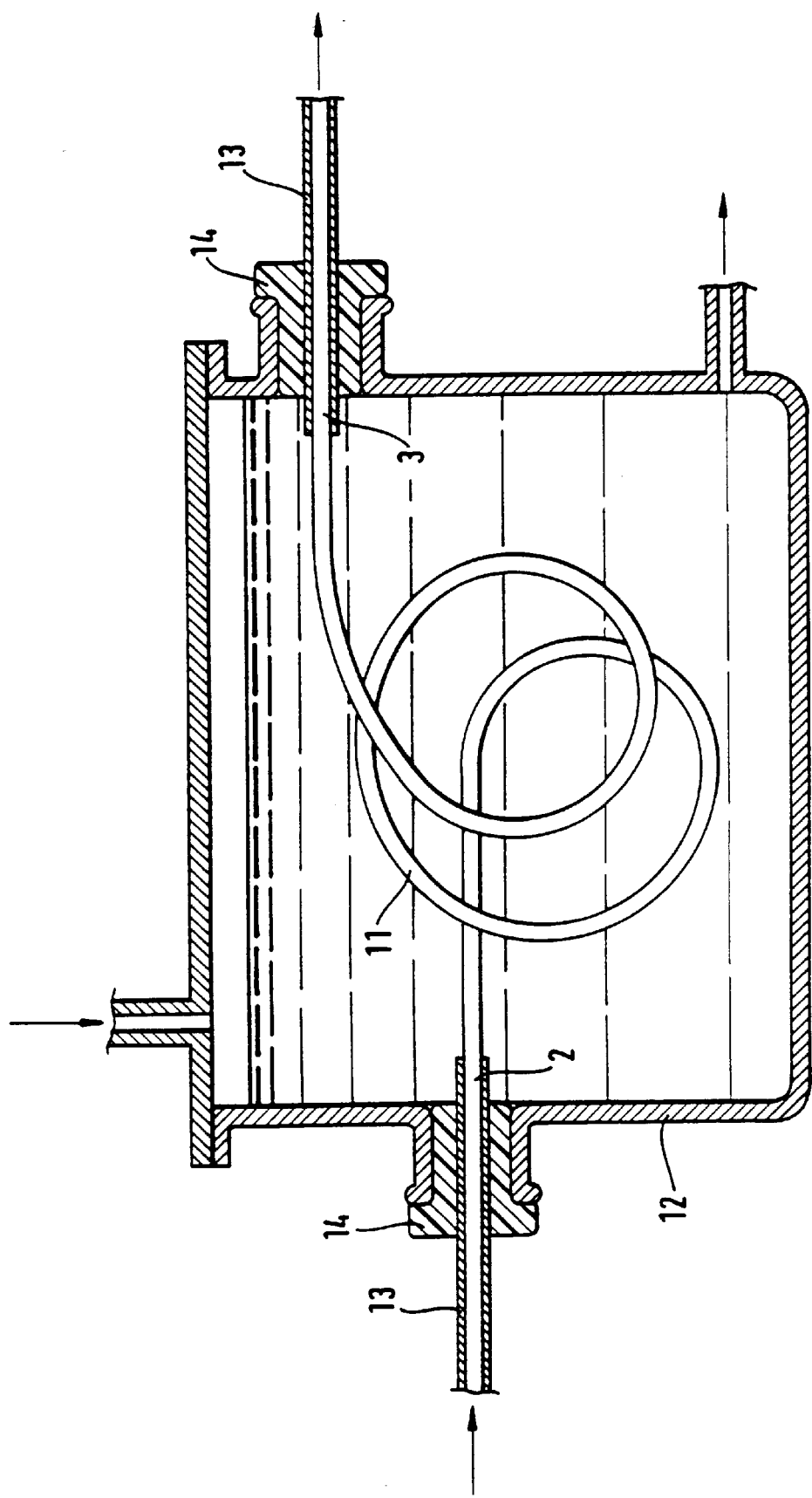
FIG. 2 shows a probe built into a continuous flow cell.

FIG. 2 represents a one-piece probe 11 which is built into a continuous flow cell 12 using stoppers 14. In this case, "one-piece" means that the feed line 2, the sensor and the exit line 3 are contained in a fiber made of an optical polymer. In the region of the feed line 2 and the exit line 3, the fiber is provided with a protective jacket 13, but not in the region which is in contact with the medium and is used as the sensor.

Figure 3:
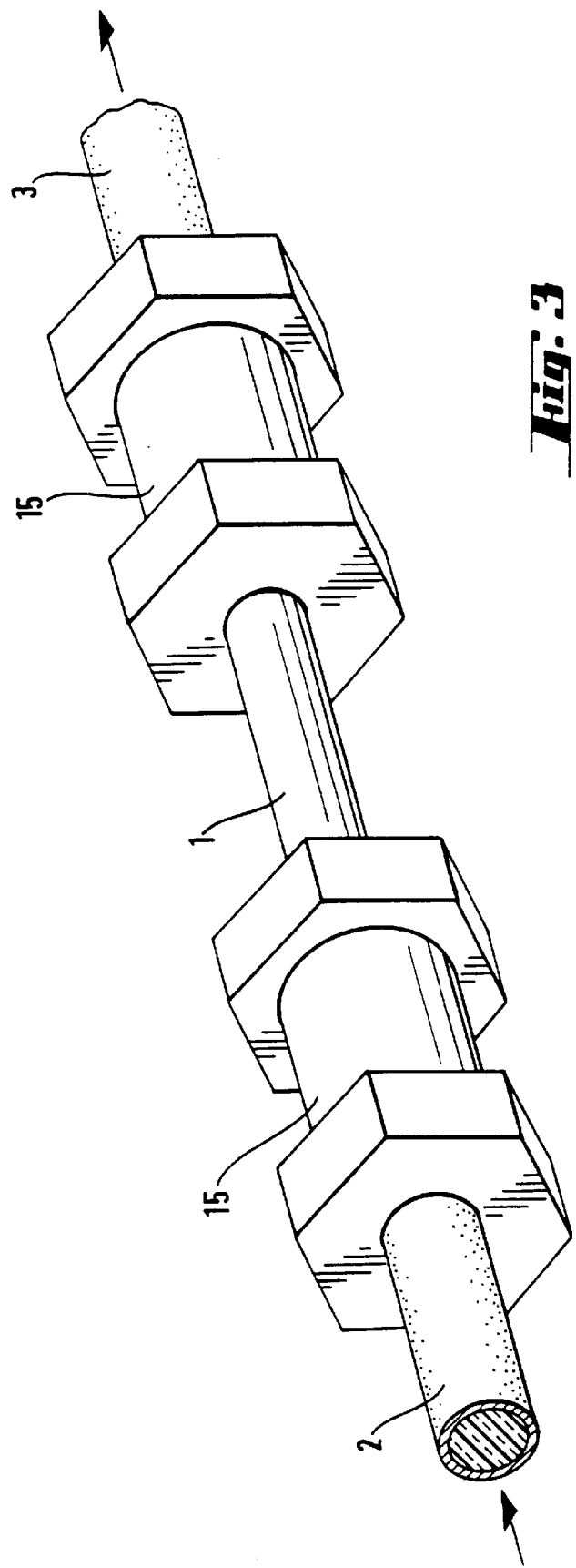
FIG. 3 shows a probe assembled from a plurality of polymers.

In FIG. 3, a sensor fiber 1 is connected to the feed line 2 and the exit line 3 via two plug connections 15, preferably FSMA plug connections.

Figure 4:
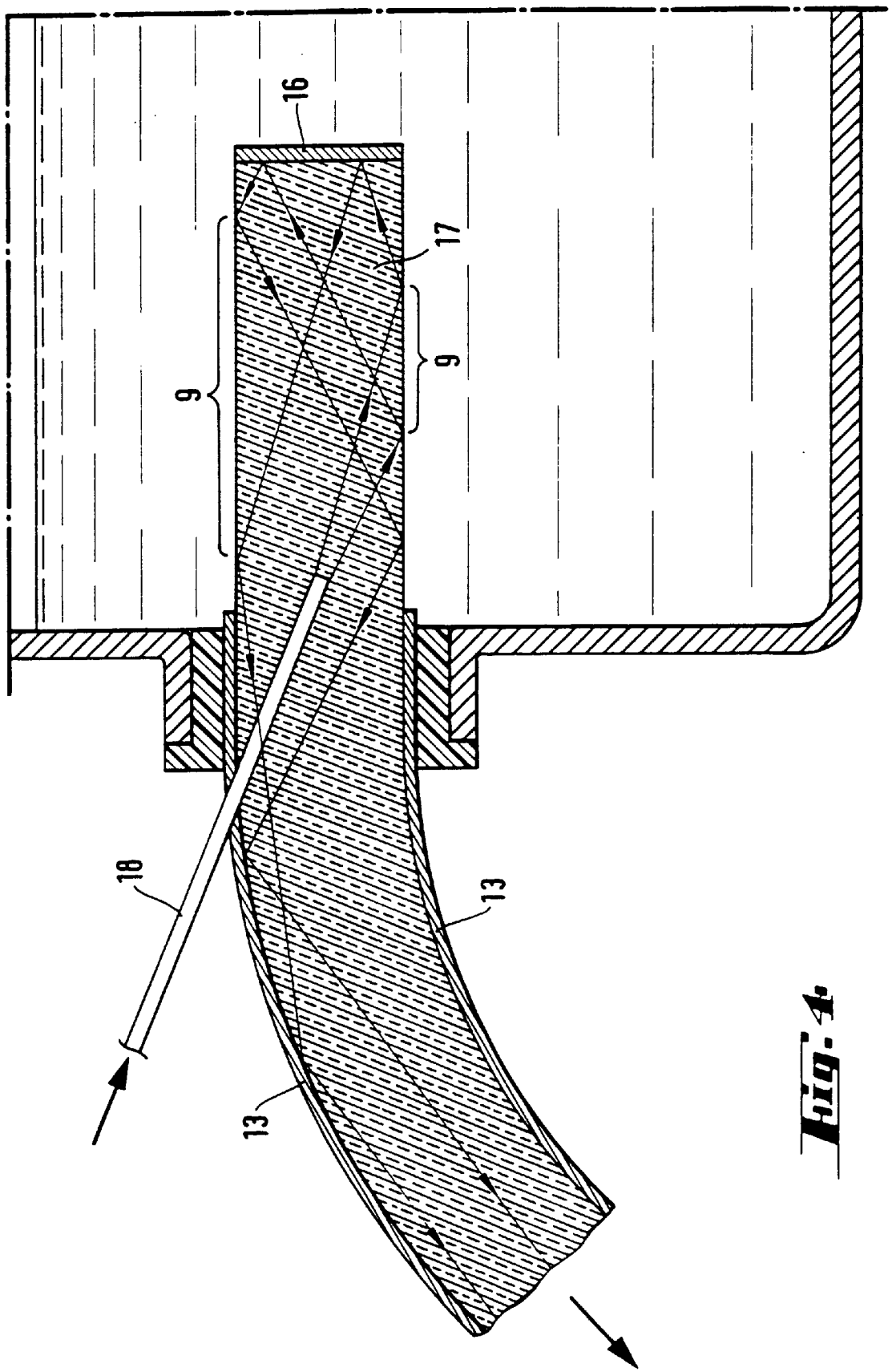
FIG. 4 shows a probe into which a glass fiber, mirrored at one end, is fused.

FIG. 4 shows a probe whose sensor 17 is provided with a mirror 16 at one end and has a glass fiber 18 fused into it, this glass fiber being used to supply the light.

The following four examples of tests are intended to illustrate the probes according to the invention more fully. The results of the four tests are in each case documented in the form of an absorption spectrum in FIGS. 5, 6a, 7a, 8a, sometimes together with the shapes of the probes according to FIGS. 6b, 7b, 8b which are used in each case.

EXAMPLE 1

A probe similar to FIG. 3 was used to measure the concentration of a black dyestuff in aqueous solution. A polymethyl methacrylate optical waveguide was used for the feed line and the exit line (2, 3). A 4 cm long rod of polycarbonate was fitted between them using FSMA connectors in such a way that the free distance between the connectors was 2 cm, the remainder being needed for the plug connection. The spectra, represented in FIG. 5, of the solution of the black dyestuff in concentrations of 100 g/l, 300 g/l and 500 g/l were measured using this probe. The extinction is in this case defined as minus the logarithm of the transmission to base ten.

EXAMPLE 2

Solutions of the same dyestuff as in Example 1 were measured using an arrangement 11 according to FIG. 6b, or corresponding to FIG. 2, but with a dyestuff concentration of 0.005, 0.1 and 1 g/l. The fiber which was used consisted of polymethyl methacrylate and was 1.2 m long, the protective jacket and the cladding having been removed over a length of 1 m. As demonstrated by the spectra in FIG. 6a, low concentrations can be measured very well using an arrangement of this type.

EXAMPLE 3

Using a one-piece probe corresponding to FIG. 2, but in a shape as outlined in FIG. 7b, solutions of the same dyestuff as in Example 1 were measured, but with a dyestuff concentration of 100, 250, 350, 450 and 500 g/l. The fiber which was used consisted of polymethyl methacrylate and was 20 cm long, the protective jacket and the cladding having been removed over a length of 1.5 cm. The characteristics of the spectra in FIG. 7a were altered by the partial light extraction at higher wavelengths with increasing concentration. These facts can be taken into account during calibration and represent a positive feature when multicomponent analysis is used.

EXAMPLE 4

FIG. 8b gives an outline of a probe embodiment similar to FIG. 3, but with a curved polycarbonate rod having a diameter of 3 mm as the sensor. It was connected by FSMA connectors to polymethyl methacrylate fibers which were used for the light to be fed in and to exit. The same dyestuff as in Example 1 was examined using a probe of this type. The spectrum in FIG. 8a shows that the dyestuff concentration measurable using this arrangement was above 1 g/l.

We claim:

1. An ATR spectrometer employing visible light and containing an optical probe having a sensor for visible light and a feed line and an exit line for light, wherein the sensor comprises at least one fiber consisting of a transparent optical polymer, the polymer being selected from the group consisting of polymethyl methacrylate, polycarbonates, polystyrenes, polyolefins, polyesters, polysulfones, polyether sulfones, polyether imides, polyarylates, polyamides, polyester carbonates, copolymers consisting of methyl methacrylate and n-pentafluoropropyl methacrylate or polymer blends of polymethyl methacrylate/polyvinylidene fluoride, or a combination thereof, and in which the light is guided in an angular range of from 0° to 40° with respect to the axis of the fiber.

2. An ATR spectrometer as claimed in claim 1, wherein the transparent optical polymer is polymethyl methacrylate.

3. An ATR spectrometer as claimed in claim 1, wherein the sensor comprises at least two fibers connected to one another by a plug connection.

4. An ATR spectrometer as claimed in claim 1, wherein the diameter of the at least one fiber ranges from 0.2 to 10 mm.

5. An ATR spectrometer as claimed in claim 1, wherein a glass fiber is fused into the at least one fiber.

6. An ATR spectrometer as claimed in claim 1, wherein the at least one fiber is mirrored at one end.

7. A method of analyzing a liquid media by means of ATR spectroscopy which comprises employing an ATR spectrometer as claimed in claim 1.

8. A method as claimed in claim 7, wherein the liquid media is a dyestuff solution.

9. A method as claimed in claim 7, wherein the liquid media is blood.

* * * * *